United States Patent [19]

Hope

[11] Plant 4,568

[45] Jul. 8, 1980

[54] KALANCHOE NAMED CONQUISTADOR

[75] Inventor: Claude Hope, Cartago, Costa Rica

[73] Assignee: Pan-American Plant Company, West Chicago, Ill.

[21] Appl. No.: 10,417

[22] Filed: Feb. 8, 1979

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new kalanchoe variety for greenhouse culture as a pot plant and suitable for year around flowering with a 10-week response under photoperiod control characterized by the orange-red color of its medium sized florets which bloom for an extended period due to a continuous flower bud development during the first several weeks of the blooming period, and by its upright growth with medium plant height, compact habit, and medium sized glossy foliage.

1 Drawing Figure

BACKGROUND OF THE NEW PLANT

My new kalanchoe cultivar was discovered by me in 1970 growing as a seedling of unidentified parentage among other plants in my breeding facilities at Cartago, Costa Rica. Because of its attractive orange-red florets, I selected this plant for propagation and reproduced it by means of cuttings from the original plant. I carried on propagation of this plant through several successive generations at Cartago, Costa Rica, and observed that its distinctive characteristics held true from generation to generation and appear to be firmly fixed. The origin of this cultivar is identified in my records as Seedling #16-9-5 and commercial scale propagation by means of vegetative cuttings is now being done at West Chicago, Ill., and at Parrish, Fla.

DESCRIPTION OF THE DRAWING

My new kalanchoe plant is illustrated by the accompanying photographic drawing which shows the growth and flower display characteristics of the new plant, as well as the flower color, which is shown as nearly true as it is reasonably possible to obtain by conventional full-color photographic procedures.

DESCRIPTION OF THE NEW PLANT

The following is a detailed description of my new kalanchoe cultivar with color designations according to The R.H.S. Colour Chart published by The Royal Horticultural Society of London, England, in collaboration with The British Colour Council.

THE PLANT

Origin: Seedling.

Parentage: Unidentified.

Classification:

*Botanic.*—*Kalanchoe blossfeldiana.*

*Commercial.*—Kalanchoe flowering pot plant.

Form: Upright bush.

Height: 18 to 24 cm.

Growth: Sturdy with very good strength and medium vigor.

Branching: Normal under natural conditions.

Foliage:

*Leaf size.*—Medium, about 5.1 to 9.1 cm. long and about 3.2 to 6.1 cm. wide.

*Shape.*—Ovate with sinuate margins and obtuse apex.

*Texture.*—Thick, fleshy and smooth.

*Surface aspect.*—Glossy.

*Venation.*—Pinnate.

*Color.*—Upper side — 147A, 147B. Under side — 138B.

Petioles.—About 0.9 to 1.4 cm. long.

THE BUD

Size:

*Diameter.*—About 2.5 3.0 mm.

*Length.*—About 10 to 11 mm.

Opening rate: Fast; bud opens fully within one day.

Sepals: 4, surrounding the receptacle.

*Appearance.*—Spear-shaped and upstanding.

*Surface texture.*—Smooth.

*Aspect.*—Shiny.

*Color.*—Inside surface — 144A. Outside surface — 144A.

THE FLOWER

Recommended flowering: Year around with photoperiod control.

Response: 10-week.

Natural flowering season: November through January under Costa Rican environmental conditions.

Blooms: Flower type — Regular and complete.

*Borne.*—On a compound cyme.

*Size.*—Medium. About 12 to 14 mm. in diameter and about 11 to 13 mm. in depth.

*Shape.*—Somewhat flat when bloom first opens, the petals becoming reflexed as the flower matures.

*Petals.*—Number — 4 petals per flower. Form: Separate and distinct and nearly oval. Texture: Firm. Appearance: Shiny. Color:

| | Mature | Old |
|---|---|---|
| Upper side: | 43A | 41A |
| Reverse side: | 162C | 162C |

*Tonality at a distance of* 6 *feet.*—43B

*Discoloration.*—Moderate fade after full bloom.

Peduncle: Sturdy and upright.

*Surface texture.*—Smooth.

*Color.*—146C.

Persistence: Flowers hang on and dry.

Effect of weather: None. Recommended only for greenhouse culture.

Disease resistance: This plant has been observed to resist powdery mildew in environments where that disease is present.

Fragrance: Typical kalanchoe.

Lasting quality: About 4 weeks on the blooming plant.

REPRODUCTIVE ORGANS

Stamens: Number — 8.

*Anthers.*—Color — yellow.

*Filaments.*—Color — yellow-green.

*Pollen.*—Color — yellow.

Pistils: 4 in number.

*Stigmas.*—Color—yellow-green.

Ovaries: 4 in number, each developing multiple seeds.

This kalanchoe cultivar is particularly characterized by its dark orange-red florets which exhibit moderate fading upon aging and which range from 12 to 14 mm. in diameter. This plant is further distinguished by its year-around flowering capability under photoperiod control with a uniform 10-week flowering response, by an extended blooming period for the flowering plant due to a continuous flower bud development during the first few weeks of the blooming period, by a compact growth habit and the medium height of the flowering plant, and by its medium sized glossy foliage.

I claim:

1. A new and distinct kalanchoe cultivar, substantially as herein shown and described, characterized by the orange-red coloration of its medium sized blooms, by its compact growth habit, and by the medium height of the flowering plant.

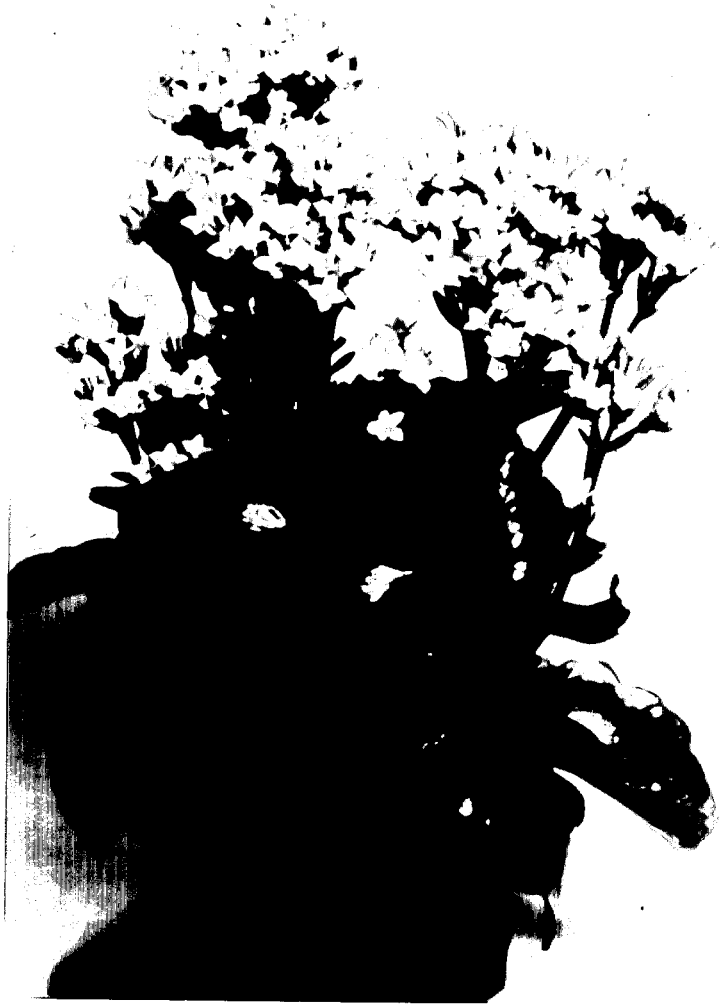

* * * * *